US 6,419,627 B1

(12) United States Patent
Ben Nun

(10) Patent No.: US 6,419,627 B1
(45) Date of Patent: Jul. 16, 2002

(54) OPHTHALMIC ENDOSCOPE AND ENDOSCOPE ATTACHMENTS FOR USE THEREWITH

(75) Inventor: Yehoshua Ben Nun, Vikit (IL)

(73) Assignee: One Way Ocular Technology, Ltd., Ramat Gan (IL)

(*) Notice: Subject to any disclaimer, the term of this patent is extended or adjusted under 35 U.S.C. 154(b) by 0 days.

(21) Appl. No.: 09/463,711
(22) PCT Filed: Jul. 31, 1998
(86) PCT No.: PCT/IL98/00362
§ 371 (c)(1),
(2), (4) Date: Mar. 23, 2000
(87) PCT Pub. No.: WO99/05997
PCT Pub. Date: Feb. 11, 1999

(30) Foreign Application Priority Data

Aug. 1, 1997 (IL) .................................................. 121450

(51) Int. Cl.⁷ .................................................. A61B 1/04
(52) U.S. Cl. ....................... 600/125; 600/124; 600/117; 606/4
(58) Field of Search ................................. 600/125, 124, 600/181, 117, 108, 182; 606/4

(56) References Cited

U.S. PATENT DOCUMENTS

| | | | | |
|---|---|---|---|---|
| 4,607,622 A | * | 8/1986 | Fritch et al. .................... 128/6 |
| 4,825,259 A | * | 4/1989 | Berry, Jr. ..................... 356/241 |
| 4,905,082 A | * | 2/1990 | Nishigaki et al. .............. 358/98 |
| 5,121,740 A | * | 6/1992 | Uram ............................... 128/6 |
| 5,334,183 A | * | 8/1994 | Wuchinich .................... 606/46 |
| 5,335,648 A | * | 8/1994 | Kozawa et al. ................ 128/6 |
| 5,396,366 A | * | 3/1995 | Brown et al. ................ 359/435 |
| 5,402,768 A | * | 4/1995 | Adair ............................. 128/4 |
| 5,441,496 A | * | 8/1995 | Easley et al. ................. 606/15 |
| 5,514,125 A | * | 5/1996 | Lasser et al. ................... 606/4 |
| 5,573,493 A | * | 11/1996 | Sauer et al. ................. 600/121 |
| 5,575,754 A | * | 11/1996 | Konomura ................... 600/117 |
| 5,632,740 A | * | 5/1997 | Koch et al. .................... 606/4 |
| 5,651,783 A | * | 7/1997 | Reynard ......................... 606/4 |
| 5,879,289 A | * | 3/1999 | Yarush et al. ............... 600/109 |
| 5,935,141 A | * | 8/1999 | Weldon ....................... 606/167 |
| 6,004,263 A | * | 12/1999 | Nakaichi et al. ............ 600/176 |
| 6,086,530 A | * | 7/2000 | Mack .......................... 600/121 |
| 6,203,493 B1 | * | 3/2001 | Ben-Haim .................. 600/117 |

FOREIGN PATENT DOCUMENTS

DE 28 10 879 * 10/1978
DE 295 07 925 U * 7/1995

* cited by examiner

Primary Examiner—Linda C. M. Dvorak
Assistant Examiner—Jocelyn D Ram
(74) Attorney, Agent, or Firm—Nath & Associates PLLC; Gary M. Nath; Marvin C. Berkowitz

(57) ABSTRACT

Ophthalmic endoscope (1) for use with an endoscope attachment (2) having a tubular body member (18), the endoscope (1) having a rigid probe (9) on which the endoscope attachment (2) is slidingly mounted.

26 Claims, 7 Drawing Sheets

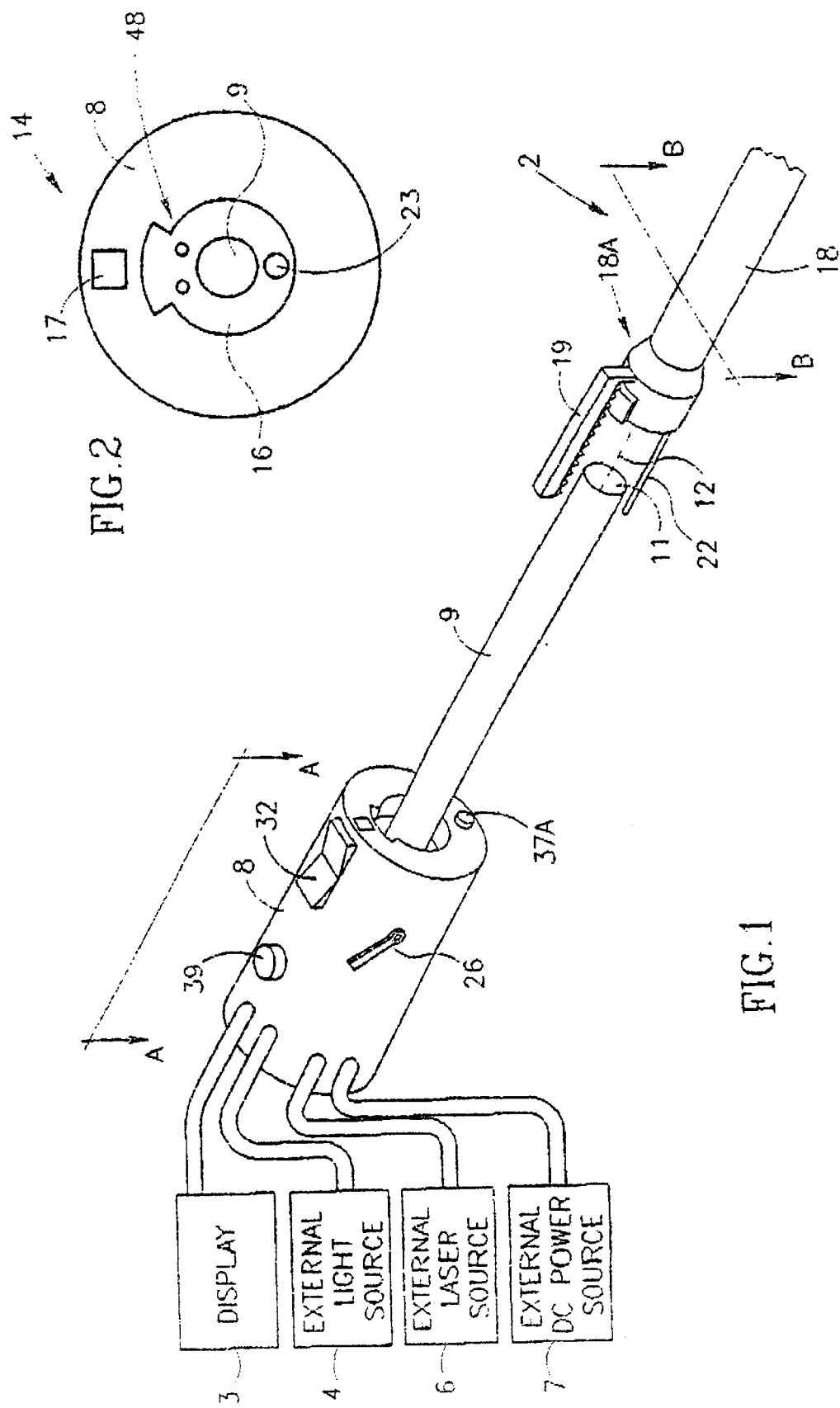

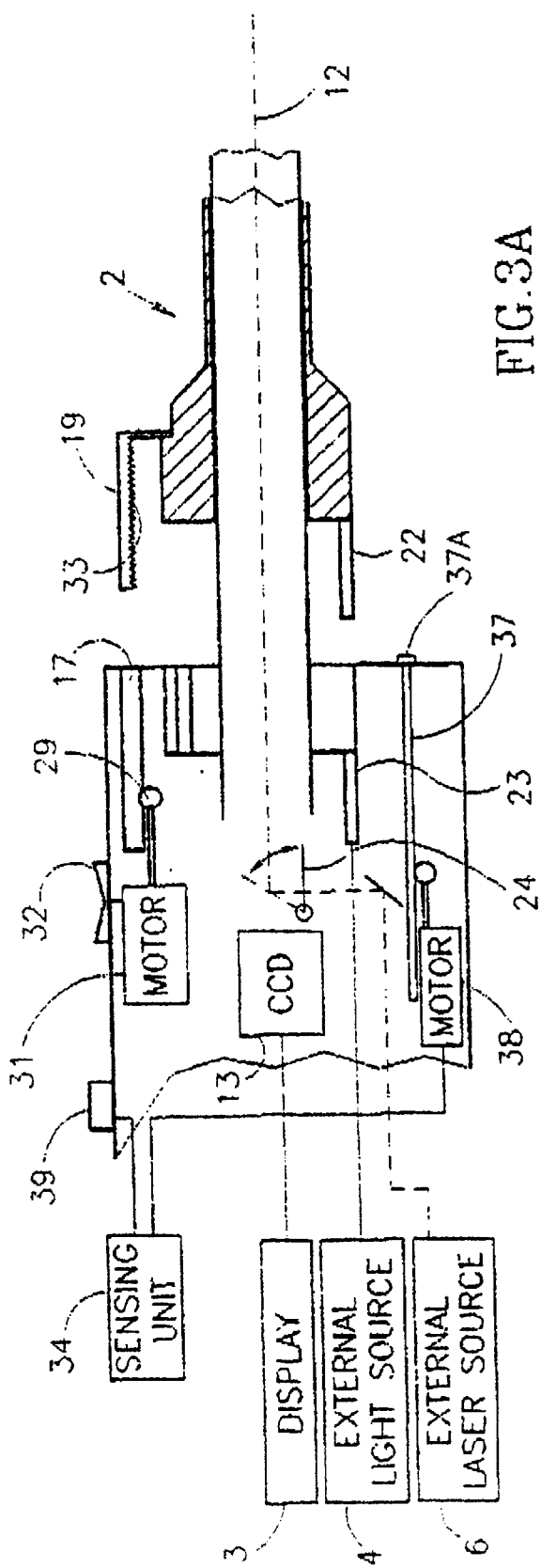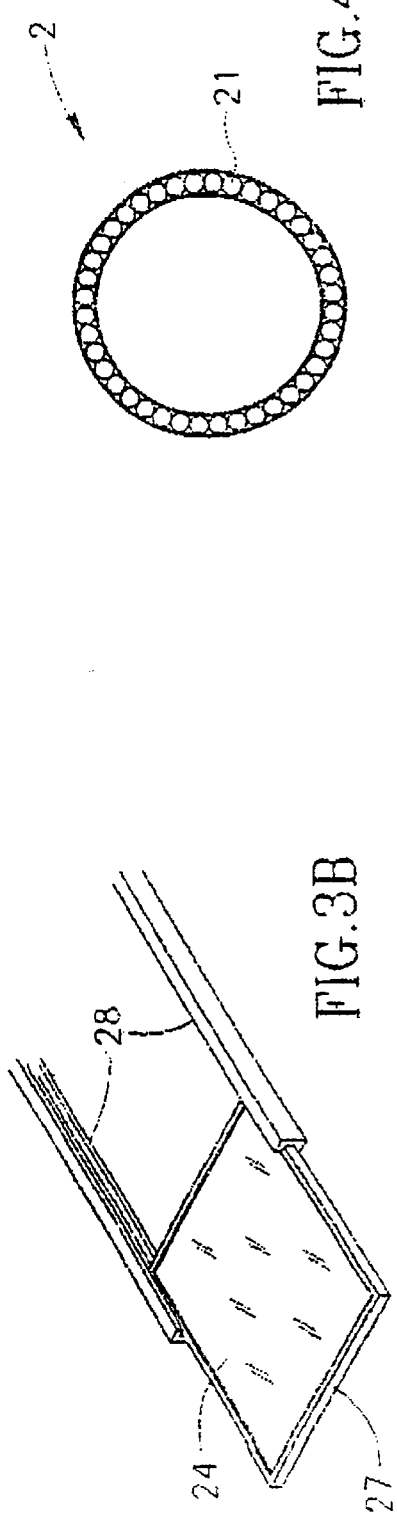

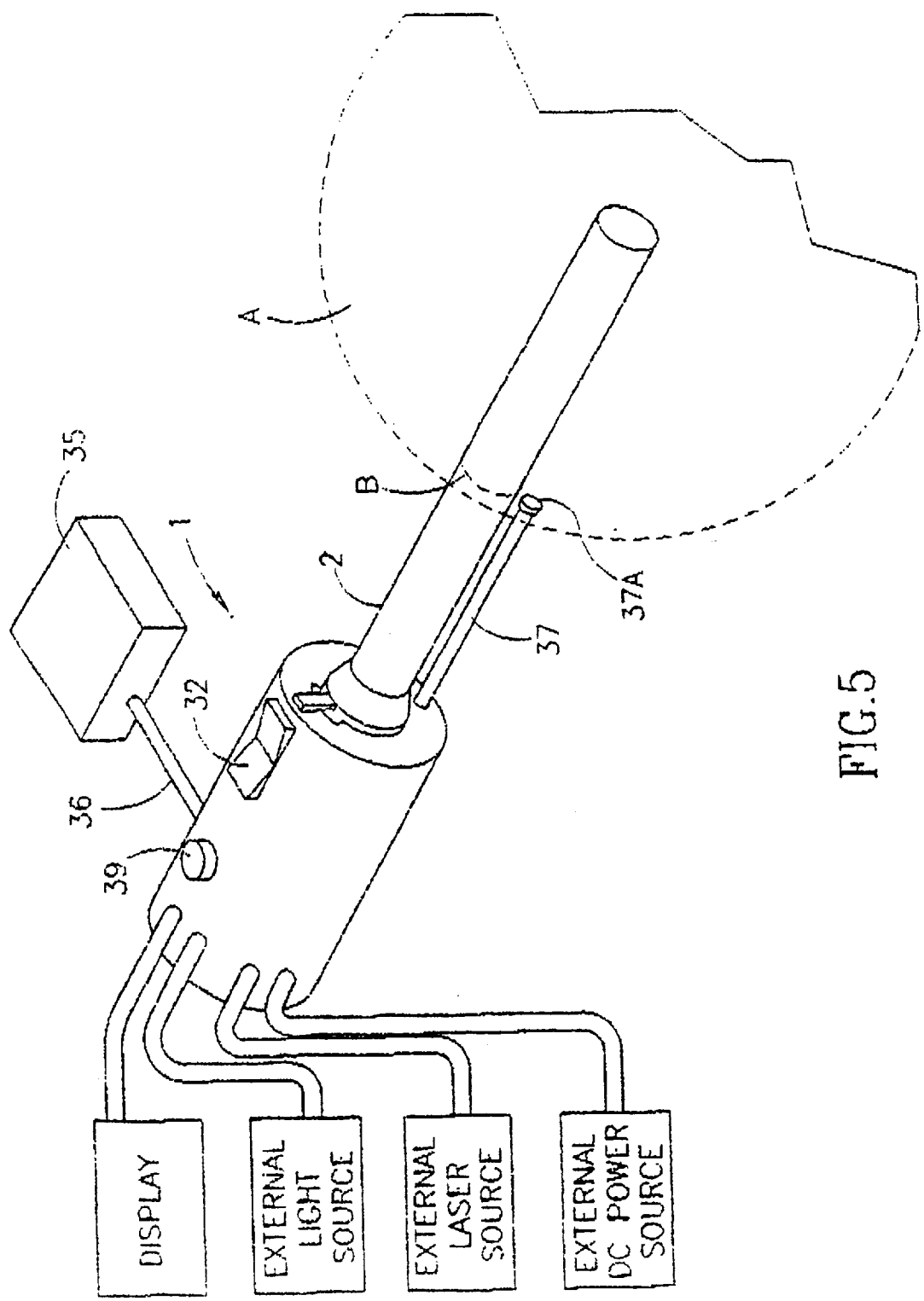

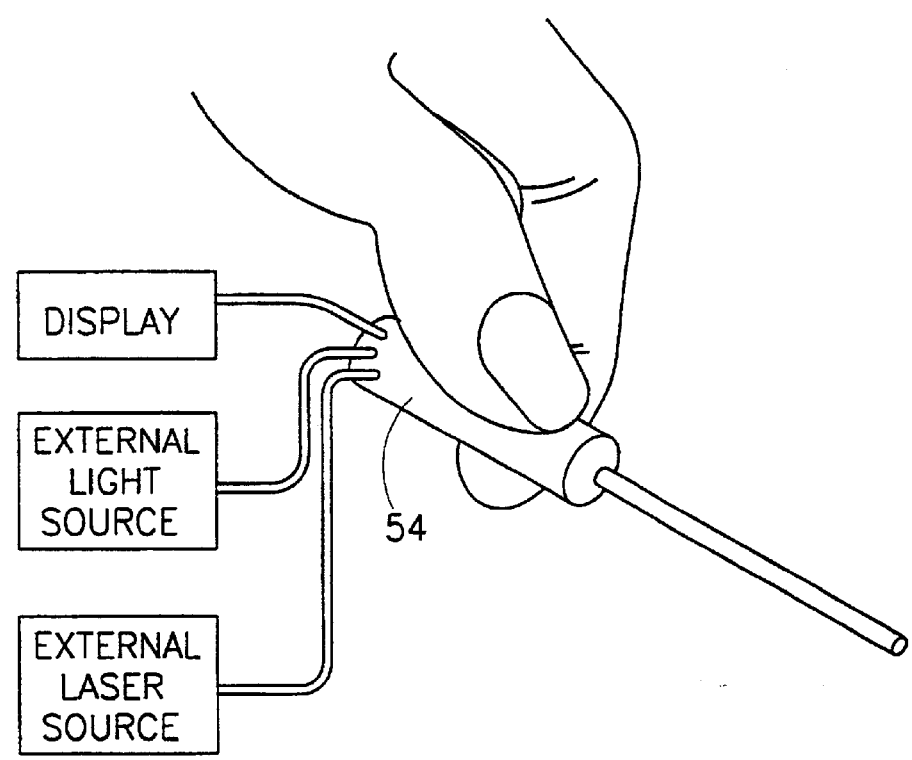
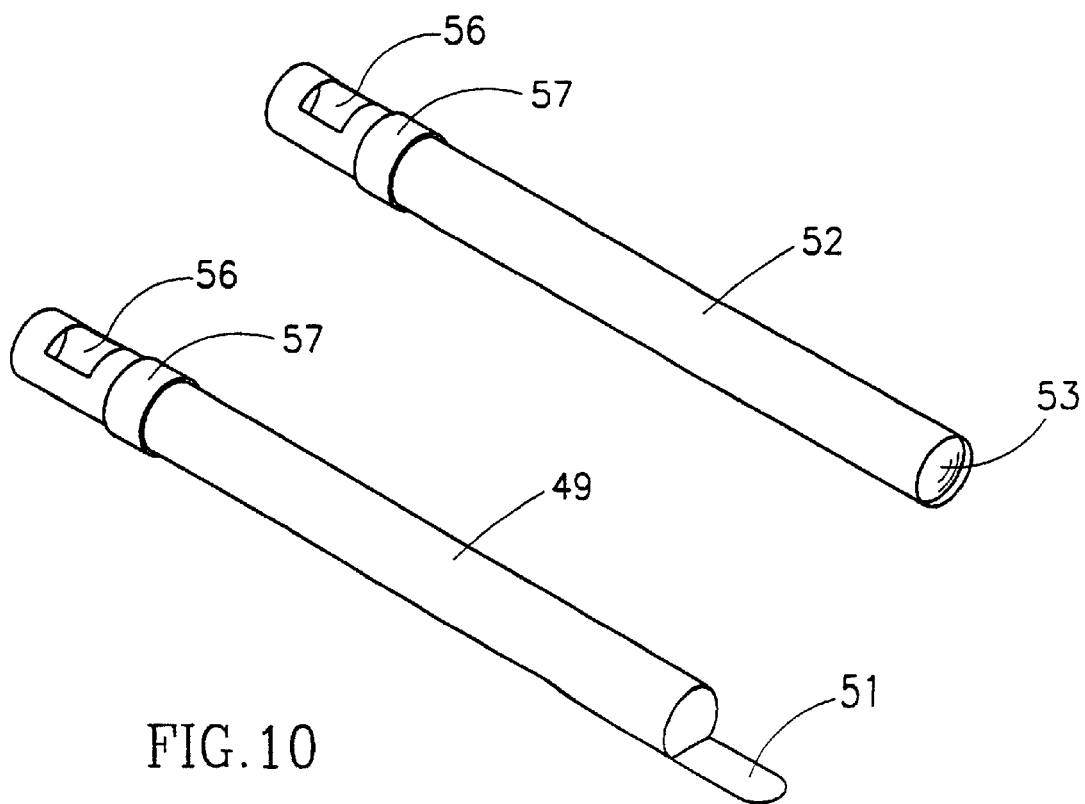
FIG.10

OPHTHALMIC ENDOSCOPE AND ENDOSCOPE ATTACHMENTS FOR USE THEREWITH

FIELD OF THE INVENTION

The invention generally relates to ophthalmic surgical equipment in general and ophthalmic endoscopes in particular.

BACKGROUND OF THE INVENTION

Ophthalmic surgical procedures typically require that two or even three surgical instruments are simultaneously deployed within the vicinity of a surgical site. The recommended diameter of an ocular surgical opening is about 1 mm which approximately corresponds to the diameter of each instrument and therefore normally two or three ocular surgical openings are required for an ophthalmic surgical procedure, each surgical opening enabling the insertion of a single instrument therethrough.

In U.S. Pat. No. 4,607,622 to Fritch, there is illustrated and described an ophthalmic endoscope provided with a probe formed with a conduit for accepting instruments, for example, a cutting device- for taking a sample (see Col. 3, lines 16–19) or fiber optics connected to an external laser source for ocular laser intervention However, in order to accommodate the conduit whilst maintaining the same endoscopic ability, the dimensions of the probe are necessarily greater tan those recommended for a surgical opening.

SUMMARY OF THE INVENTION

In accordance with a first aspect of the present invention, there is provided an ophthalmic endoscope for use with an endoscope attachment having a generally tubular body member, the endoscope comprising a rigid probe with an optical axis and a tip, and an attachment interface for releasably engaging the body member of an endoscope attachment slidingly mounted on said probe.

In accordance with a second aspect of the present invention, there is provided an endoscope attachment for use with an ophthalmic endoscope having a rigid probe with an optical axis and a tip, the endoscope attachment comprising a tubular body member for slidingly mounting on the probe.

Endoscope attachments of the present invention can be adapted for mounting on either a purpose built ophthalmic endoscope with an attachment interface or a conventional ophthalmic endoscope whereby a hitherto considered passive device is converted into a multi-purpose surgical device useful for a wide range of conventional and newly envisaged intraocular surgical procedures in various tissues of the eye. Mounting of an endoscope attachment on an ophthalmic endoscope's probe enables the imaging of a surgical procedure at high magnifications of up to 50× with an image resolution better than that obtained with an hitherto employed external imaging system i.e. an operating microscope.

For use with the purpose built ophthalmic endoscope of the present invention, the endoscope attachments preferably have a tubular body member coextensive with the endoscope probe when mounted thereon, the body member having longitudinally directed optic fibers for transmitting illumination light therealong for illumination of a surgical site. The overall width of the probe together with an endoscope attachment mounted thereon is about 1 mm for insertion through a conventional sized ocular surgical opening. In addition, an endoscope attachment can include surgery associated means typically disposed beyond the probe tip when mounted on the probe, the surgery associated means being implemented as an optical element for ocular examination, a surgical tip for ocular surgical intervention or a cauterization tip for ocular cauterization intervention. The ophthalmic endoscope of the present invention can be implemented for selectively displacing the surgical associated means relative to the probe along its optical axis whereby surgical procedures can be performed whilst maintaining the same field of view and image features. The ophthalmic endoscope of the present invention can be implemented for use with a computer controlled XYZ manipulator for facilitating magnifications greater than ×100.

BRIEF DESCRIPTION OF THE DRAWINGS

In order to understand the invention and how it is used, preferred embodiments will now be described by way of non-limiting examples only, with reference to the accompanying drawing in which:

FIG. 1 is a pictorial view of an ophthalmic endoscope with an endoscope attachment for use therewith in accordance with the present invention;

FIG. 2 is a front view of the endoscope of FIG. 1;

FIG. 3A is a longitudinal cross section of the ophthalmic endoscope of FIG. 1 along line A—A;

FIG. 3B is a close-up view up of an interchangeable dichroic mirror of the ophthalmic endoscope of FIG. 1;

FIG. 4 is a transverse cross section of the endoscope attachment of FIG. 1 along line B—B;

FIG. 5 is a pictorial view of the ophthalmic endoscope of FIG. 1 held and manipulated by a computer controlled XYZ manipulator;

FIG. 10 is a perspective view of a conventional ophthalmic endoscope with an endoscope attachment in accordance with the present invention;

DETAILED DESCRIPTION OF DRAWINGS

Figure 6:
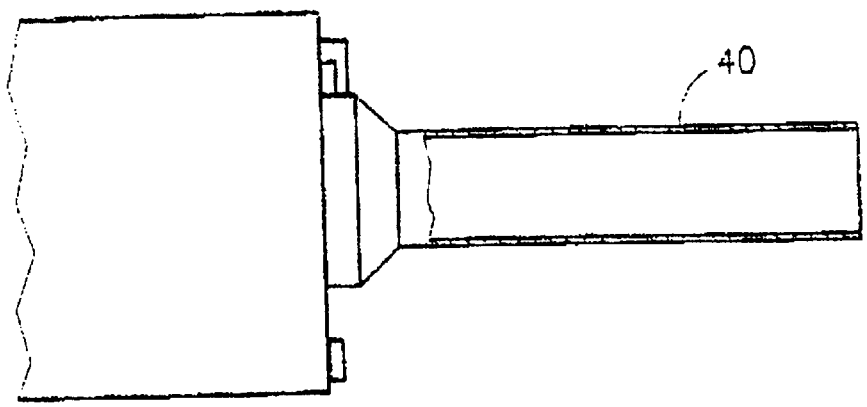
FIGS. 6–9 are partially cut-away side views of the ophthalmic endoscope of FIG. 1 with different endoscope attachments.

In FIGS. 1–3, an ophthalmic endoscope 1 is adapted for use with an endoscope attachment 2 and for connection to a display 3, an external light source 4, an external laser source 6 and an external DC power source 7. The endoscope 1 has a handpiece 8 and a rigid probe 9 having a tip 11 and defining an optical axis 12 on which a CCD 13 is disposed for imaging a surgical site on the display 3.

The handpiece 8 has an attachment interface 14 constituted by a major socket 16 from whose center the probe 9 extends and a minor socket 17, the major socket 16 being adapted for securely engaging a proximal end 18A of a tubular sleeve-like body member 18 of the endoscope attachment 2 and the minor socket 17 being adapted to receive a rearwardly directed tang 19 of the endoscope attachment 2. The endoscope attachment's body member 18 is shaped and dimensioned for tight sliding along the probe 9 and contains a fiber optic annulus 21 (see FIG. 4) which is coupled via a pin 22 received in a socket 23 connected to the external light source 4 for transmitting illumination light therealong for illuminating an eye's interior.

The handpiece 8 has a dichroic flip flop mirror 24 under the control of a hand operated external lever 26 for selectively enabling laser light from the external laser source 6 to be transmitted along the probe 9 when disposed along the optical axis 12. The flip flop mirror 24 is releasably held in a carriage 27 slidably mounted on tracks 28 such that the flip flop mirror 24 is interchangeable whereby different lasers can be employed The handpiece 8 has a cog 29 driven by a motor 31 under the control of a hand operated rocker switch 32 for engaging a rack 33 formed on the tang's underside for selectively displacing the endoscope attachment 2 relative to the probe 9 along a stroke of about 3 mm whereby surgical procedures can be performed whilst maintaining the same field of view and image features.

The ophthalmic endoscope 1 has a sensing unit 34 for use with a computer controlled XYZ manipulator 35 (see FIG. 5) supporting the handpiece 8 by means of a support rod 36. The sensing unit 34 has a sensor 37 reciprocatingly extendable in a direction parallel to the optical axis 12 between a fully retracted position when it is substantially flush with the handpiece's front surface and a fully protruding position when it is substantially coextensive with the probe tip 11. The sensor 37 is initially fully extended by a motor 38 on depressing a pushbutton 39 and thereafter its tip 37A is continuously urging against a portion of an eye wall A adjacent an ocular surgical opening B through which a surgical procedure is performed. During such a procedure, the XYZ manipulator 35 utilizes the distance of the sensor's tip 37A from its fully retracted position as sensed by the sensing unit 34 for manipulating the endoscope 1 relative to the ocular surgical opening B in a manner similar to a ball and socket like universal socket.

Figure 7:
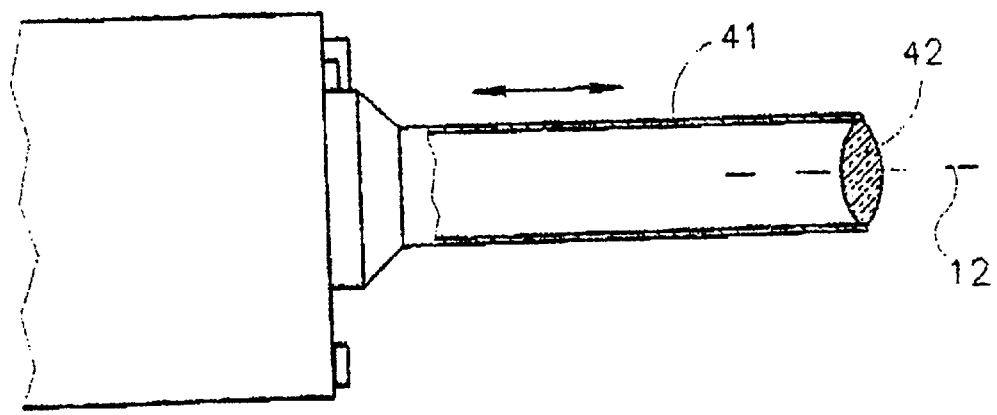
Figure 8:
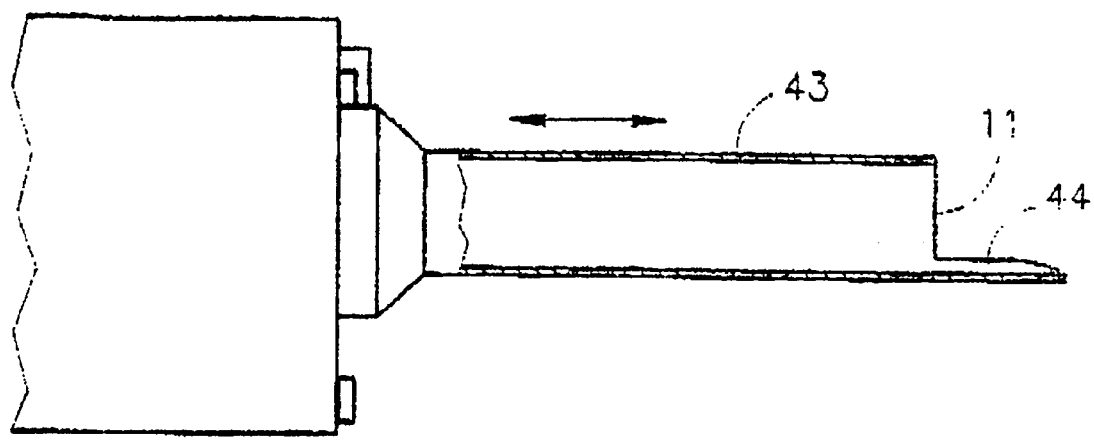
Figure 9:
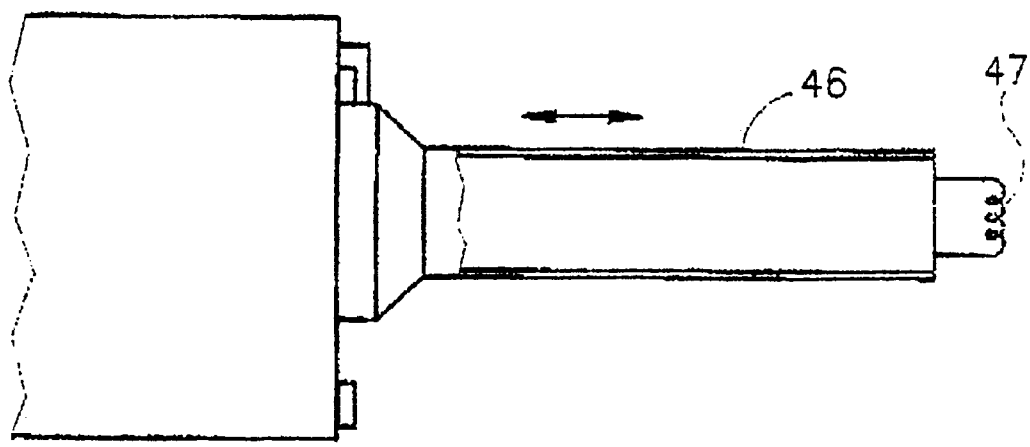

The ophthalmic endoscope 1 is adapted for use with a number of different endoscope attachments 2, the simplest attachment 40 (see FIG. 6) thereof being similar to the endoscope attachment 2 except without the tang 19 suitable for ocular examination and ocular laser intervention. Other attachments with a tang enabling selective displacement relative to the and including surgical associated means at their distal ends are as follows: An endoscope attachment 41 thereto (see FIG. 7) with an optical element 42 disposed along the optical axis 12 on its mounting suitable for ocular examination and ocular laser intervention. An endoscope attachment 43 (see FIG. 8) with a surgical tip 44 extending beyond the probe tip 11 in a bayonet-like fashion on its mounting suitable for ocular surgical intervention. An endoscope attachment 46 (see FIG. 9) with a cauterization tip 47 coupled to an electrical coupling 48 (see FIG. 2) connected to the external DC power source 8 extending beyond the probe tip 11 in a bayonet-like fashion suitable for ocular cauterization intervention.

Figure 11:
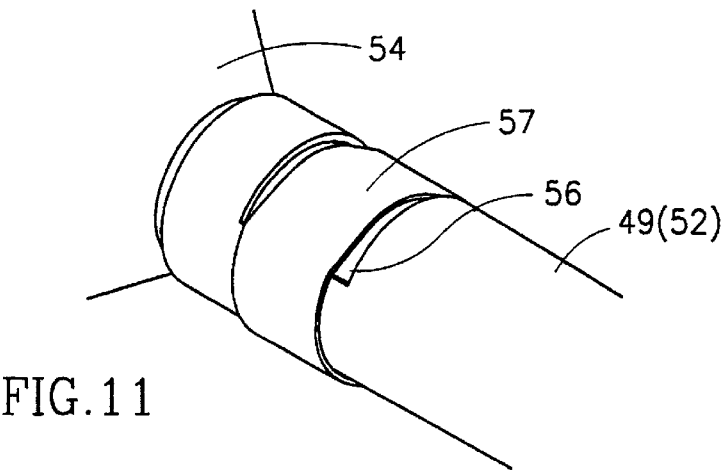
FIG. 11 is a close-up view showing the mode of attachment of an endoscope attachment to a conventional endoscope attachment.

In FIG. 10, an endoscope attachment 49 with a surgical blade 51 or an endoscope attachment 52 with an optical element 53 can be slidably mounted on aconventional ophthalmic endoscope 54, each endoscope attachment 49 and 52 having a slit 56 transverse to its longitudinal axis whereby it secured to the endoscope's probe by means of an elastic member 57 circumscribing the probe surface exposed through the slit 56 and the probe's outer surface (see FIG. 11).

Figure 12A:
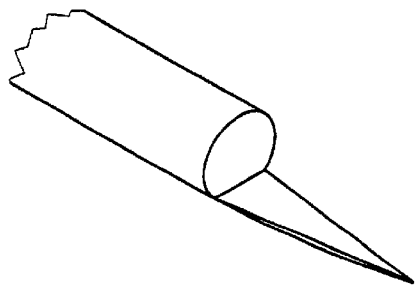
FIGS. 12A–12E are close-up views of various endoscope attachments of the present invention.
Figure 12B:
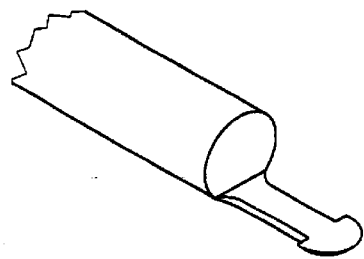
Figure 12C:
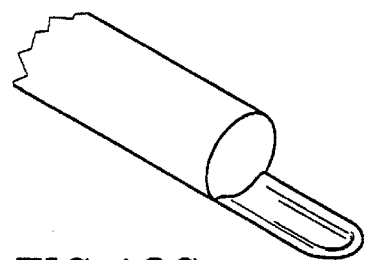
Figure 12D:
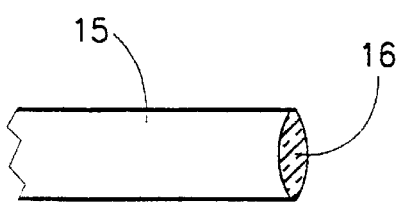
Figure 12E:
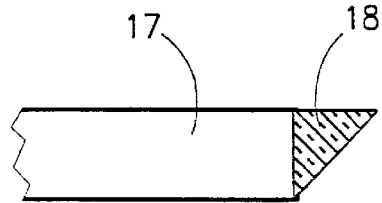

Various modifications and changes may be made in the configuration described above that come within the spirit of the invention. The invention embraces all such changes and modifications coming within the scope of the appended claims. For example, different modes of attachment between the endoscope attachments and the endoscopes can be employed. In addition, the probe 9 may include the fiber optic annulus 21. Also, a surgical tip can include a pin point shaped blade (see FIG. 12A), a crescent shaped blade (see FIG. 12B) and a round point shaped blade (see FIG. 12C) whilst an optical element can include a convex lens 16 for focusing purposes (see FIG. 12D) or a prism 18 for refracting purposes (see FIG. 12E).

What is claimed is:

1. Ophthalmic endoscope comprising a rigid probe with an optical axis and a tip, for use with an endoscope attachment having generally tubular body member, said endoscope having engaging means adapted for slidingly mounting said attachment on said rigid probe so that, when so mounted, said body is co-extensive with said probe, and for releasably engaging the body member to provide selective displacement of said attachment on said probe.

2. An endoscope according to claim 1 further comprising a dichroic optical element for selectively directing laser light along said optical axis.

3. An endoscope according to claim 2 wherein said dichroic optical element is interchangeable.

4. An endoscope according to claim 1 further comprising a light coupling for transmitting illumination light along an endoscope attachment for illumination of an eye's interior.

5. An endoscope according to claim 1, wherein said engaging means is motorized and is capable of providing said displacement within a distance enabling the use of said attachment whilst maintaining the endoscope's field of view.

6. An endoscope according to claim 1 further comprising an electrical coupling for energizing a cauterization tip of an endoscope attachment for ocular cauterization intervention.

7. An endoscope according to claim 1 further comprising a sensor selectively urgeable against an eye wall during an ophthalmic surgical procedure.

8. An endoscope according to claim 7 wherein said sensor is extendable in a direction substantially parallel to said optical axis.

9. An endoscope according to claim 1 wherein said rigid probe includes an optic core and a fiber optic annulus in a cross section thereof perpendicular to said probe axis.

10. An endoscope attachment for use with an ophthalmic endoscope having a rigid probe with an optical axis and a tip and having an attachment interface, the endoscope attachment comprising a generally tubular body member shaped and dimensioned for mounting on and tight sliding along said probe so as to be co-extensive with said probe when mounted thereon, and engaging means for engaging said attachment interface so as to enable selective displacement of said attachment along said probe.

11. An endoscope attachment according to claim 10 wherein said body member has longitudinally directed fiber optics for transmitting illumination light therealong for illumination of an eye's interior, when the attachment is mounted on said probe.

12. An endoscope attachment according to claim 10 further comprising surgery associated means disposed beyond the probe tip when said attachment is mounted on the probe.

13. An endoscope attachment according to claim 12 wherein said surgery associated means includes an optical element for ocular examination.

14. An endoscope attachment according to claim 12 wherein said surgery associated means includes a surgical tip for ocular surgical intervention.

15. An endoscope attachment according to claim 12 wherein said surgery associated means includes a cauterization tip for ocular cauterization intervention.

16. A multi-purpose ophthalmic endoscope system comprising an ophthalmic endoscope having a rigid probe with an optical axis and a tip, and a plurality of different endoscope attachments each having a generally tubular body member slidingly mountable on said rigid probe so as to be co-extensive therewith, said endoscope and said attachments having engaging means for releasably interacting with each other in such a manner as to enable selective displacement of each attachment on said probe.

17. A multi-purpose ophthalmic endoscope system according to claim 16, wherein said engaging means is motorized.

18. A multi-purpose ophthalmic endoscope system according to claim 16, wherein said engaging means is adapted to provide said displacement within a distance enabling the use of said attachment whilst maintaining the endoscope's field of view.

19. A multi-purpose ophthalmic endoscope system according to claim 16, wherein at least one of said attachments has an operative tip at a distal end of said body member, selected from a group consisting of an optical element for ocular examination and ocular, laser intervention, a surgical tip for ocular surgical intervention, and a cauterization tip for ocular cauterization intervention.

20. A multi-purpose ophthalmic endoscope system according to claim 19, wherein said attachments are adapted for mounting on said probe so as to dispose their operative tips in the vicinity of the tip of said probe.

21. A multi-purpose ophthalmic endoscope system according to claim 20, wherein at least one of said attachments is adapted for mounting on said probe so as to dispose its operative tip beyond the tip of said probe.

22. An ophthalmic endoscope comprising a rigid probe with an optical axis and a tip, for use with an endoscope attachment having generally tubular body member adapted to be slidingly mounted on said rigid probe, said endoscope having engaging means for releasably engaging said body member and for selectively displacing said attachment on said probe within a distance enabling the use of said attachment whilst maintaining the endoscope's field of view.

23. An ophthalmic endoscope system comprising an ophthalmic endoscope having a rigid probe with an optical axis and a tip, and at least one endoscope attachment having a generally tubular body member adapted to be slidingly mounted on said rigid probe, said endoscope and said attachment having engaging means adapted to interact with each other so as to provide for selective displacement of said attachment on said probe within a distance enabling the use of said attachment whilst maintaining the endoscope's field of view.

24. An ophthalmic endoscope according to claim 23, comprising a plurality of the endoscope attachments.

25. An ophthalmic endoscope system according to claim 23, wherein said attachment has an operative tip at a distal end thereof, selected from a group consisting of an optical element for ocular examination and ocular laser intervention, a surgical tip for ocular surgical intervention, and a cauterization tip for ocular cauterization intervention.

26. An ophthalmic endoscope system according to claim 23, wherein said attachment is adapted for mounting on said probe so as to dispose an operative tip thereof beyond the tip of said probe.

* * * * *